US012688917B2

(12) United States Patent　　　　　(10) Patent No.: US 12,688,917 B2

Hoffman　　　　　　　　　　　　　　　(45) Date of Patent:　　Jul. 21, 2026

(54) METHODS AND SYSTEMS FOR TAILING COLLECTION

(71) Applicant: Express Scripts Strategic Development, Inc., St. Louis, MO (US)

(72) Inventor: Robert E. Hoffman, Linden, IN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 18/542,661

(22) Filed: Dec. 16, 2023

(65) Prior Publication Data

US 2024/0120059 A1　　Apr. 11, 2024

Related U.S. Application Data

(60) Continuation of application No. 17/402,700, filed on Aug. 16, 2021, now Pat. No. 11,984,210, which is a division of application No. 15/404,425, filed on Jan. 12, 2017, now Pat. No. 11,120,105.

(51) Int. Cl.
　　*G16H 20/13*　　　(2018.01)
　　*B65B 1/02*　　　　(2006.01)
(52) U.S. Cl.
　　CPC .............. *G16H 20/13* (2018.01); *B65B 1/02* (2013.01)
(58) Field of Classification Search
　　CPC .......... G16H 20/13; B65B 1/02; B65B 55/24; A47L 5/16; G06F 19/3462
　　See application file for complete search history.

(56) References Cited

U.S. PATENT DOCUMENTS

| | | | |
|---|---|---|---|
| 4,058,953 A | * | 11/1977 | Sanborn, Jr. .......... B65B 31/021 53/511 |
| 4,931,141 A | | 6/1990 | Shafranski |
| 5,322,232 A | | 6/1994 | Freeman |
| 5,555,701 A | | 9/1996 | Fehringer |
| 5,593,470 A | * | 1/1997 | Shagott ..................... A47L 5/38 55/357 |
| 5,720,154 A | | 2/1998 | Lasher |
| 5,771,657 A | | 6/1998 | Lasher |
| 6,256,967 B1 | * | 7/2001 | Hebron ............... G07F 17/0042 53/437 |
| 6,282,869 B1 | | 9/2001 | Bullock |
| 6,347,847 B1 | | 2/2002 | Tiramani |
| 6,588,056 B2 | | 7/2003 | Holbrook |
| 6,769,228 B1 | | 8/2004 | Mahar |
| 7,010,899 B2 | | 3/2006 | Mcerlean |
| 7,765,776 B1 | * | 8/2010 | Leu ........................... B67B 3/00 53/411 |

(Continued)

*Primary Examiner* — Veronica Martin
(74) *Attorney, Agent, or Firm* — Dickinson Wright PLLC

(57) ABSTRACT

A pharmaceutical order filling system receives pharmaceutical orders and uses a packing device to package pharmaceutical orders. The packing device is configured with at least one cutter that generates tailings and dust. A tailing collection device is provided that collects the tailings and dust generated by the packing device into and through an intake tube and into a collection assembly. The collection assembly includes a hood with at least one air filter, a frame, and a bin removably received within the frame. The frame supports the hood and aligns the bin to be in fluid communication with the hood. A gas motive device is positioned intermediate the ends of an intake tub before the hood and is configured to suction the tailings and/or dust.

18 Claims, 8 Drawing Sheets

(56)            References Cited

U.S. PATENT DOCUMENTS

| 8,973,196 | B2 | 3/2015 | Tomasiak | |
|---|---|---|---|---|
| 2002/0162300 | A1 | 11/2002 | Nussbaumer | |
| 2004/0040264 | A1 | 3/2004 | Collida | |
| 2005/0274092 | A1* | 12/2005 | Rohret | B65B 7/2814 |
| | | | | 53/329.2 |
| 2008/0292220 | A1* | 11/2008 | Zacchi | F25D 3/14 |
| | | | | 220/592.2 |
| 2009/0133367 | A1 | 5/2009 | Gregerson | |
| 2011/0023421 | A1* | 2/2011 | Izquierdo | B65B 57/10 |
| | | | | 53/131.2 |
| 2013/0239519 | A1 | 9/2013 | Orsini | |
| 2016/0199257 | A1 | 7/2016 | Husnu | |
| 2017/0073169 | A1 | 3/2017 | Turcotte | |

* cited by examiner

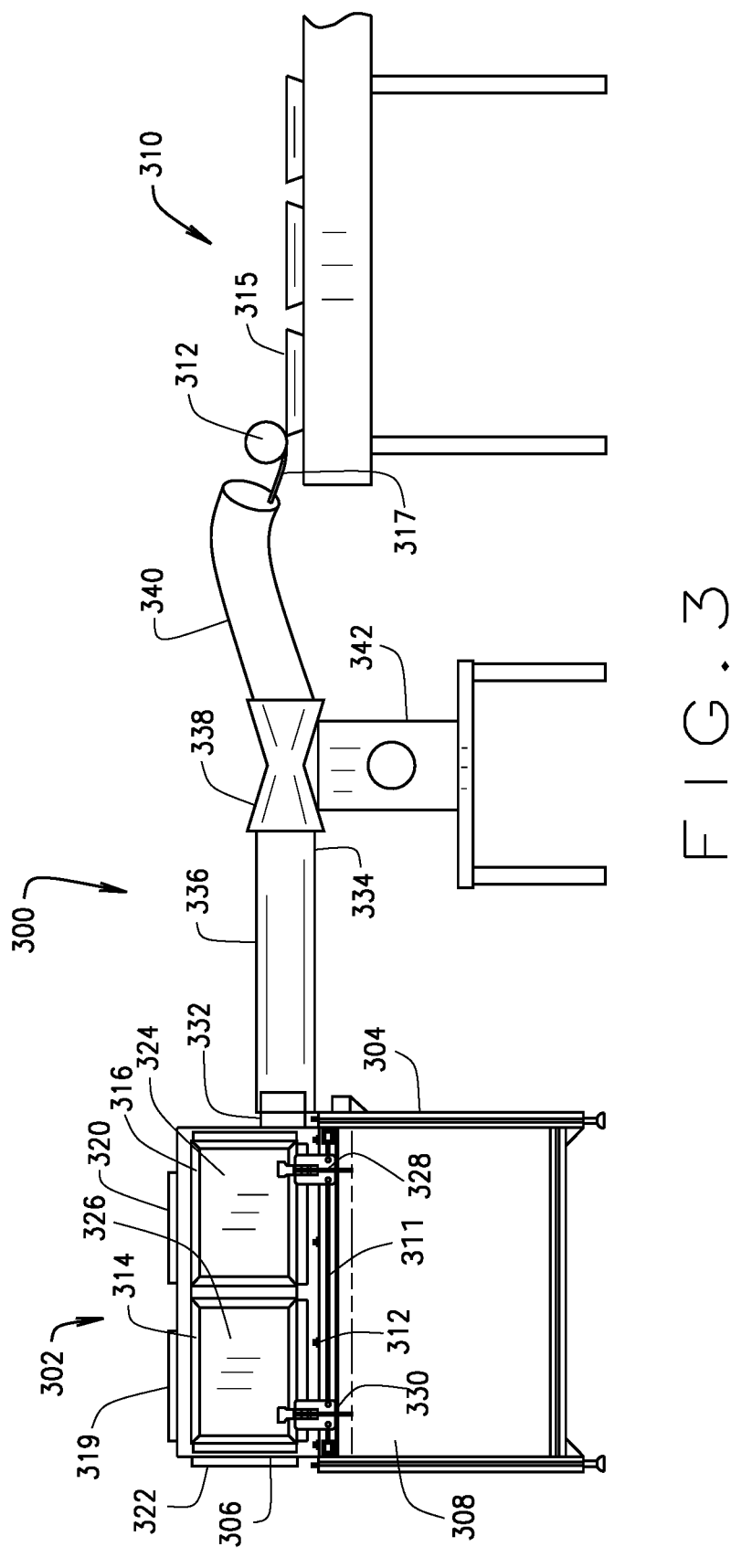
F I G . 3

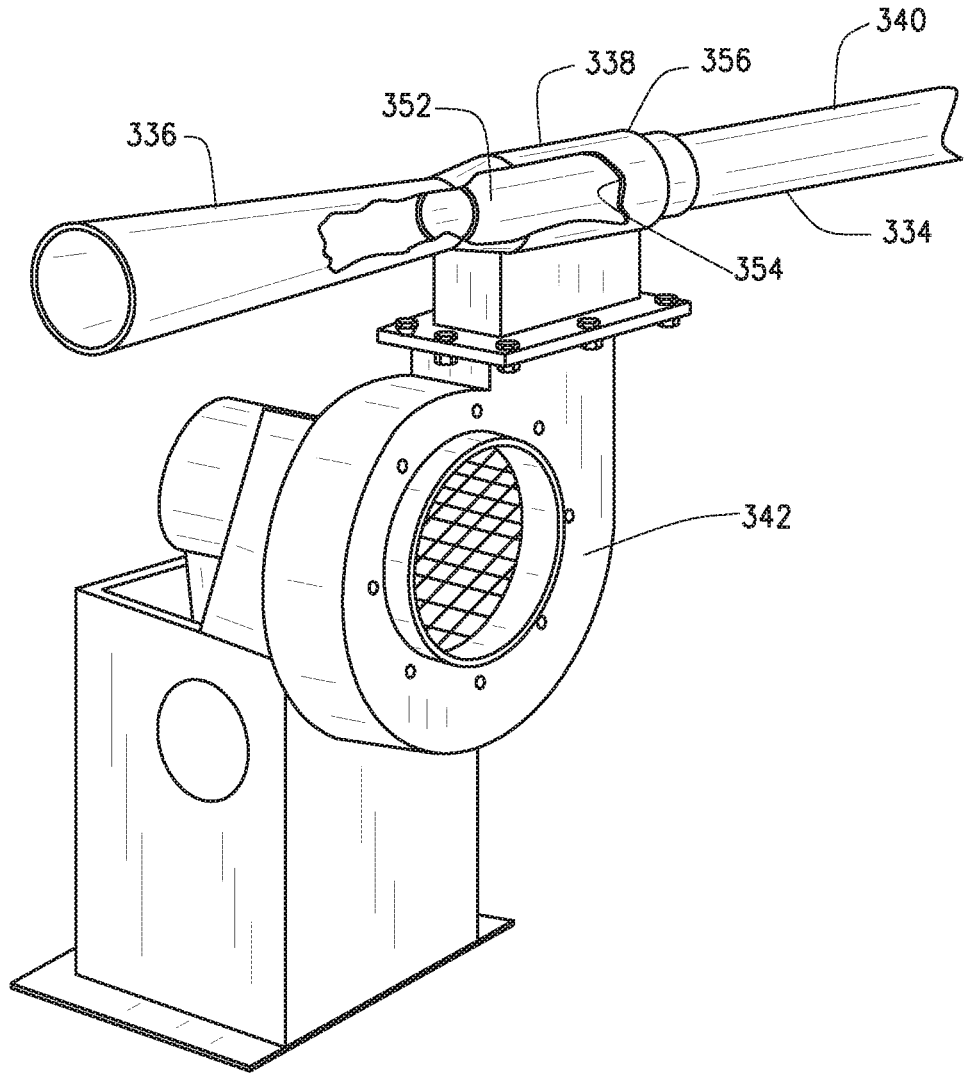
F I G . 3 B

METHODS AND SYSTEMS FOR TAILING COLLECTION

CROSS REFERENCE TO RELATED APPLICATIONS

This application is a continuation of U.S. patent application Ser. No. 17/402,700 filed on Aug. 16, 2021; said application Ser. No. 17/402,700 is a divisional application of U.S. patent application Ser. No. 15/404,425, filed on Jan. 12, 2017 and issued on Sep. 14, 2021 as U.S. Pat. No. 11,120, 105. The entire disclosure of these applications referenced above are incorporated by reference.

FIELD

The present disclosure relates generally to the technical field of automated filling centers. In a specific example, the present disclosure may relate to a high volume fulfillment center (e.g., a high volume pharmacy) and to systems and devices used in filling prescriptions and prescription orders at a high volume pharmacy.

BACKGROUND

A high-volume pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

BRIEF DESCRIPTION OF THE DRAWINGS

FIG. 3 is a side view of an example tailing collection device that may be deployed within the system of FIG. 1, according to an example embodiment;

FIG. 3B is a perspective view of a blower and a cut-away portion of an intake tube that may be deployed within the tailing collection device of FIG. 3, according to an example embodiment;

DETAILED DESCRIPTION

Example systems and methods for collecting tailings and dust generated in connection with packaging prescription orders, such as for shipment or other delivery. In the following description, for purposes of explanation, numerous specific details are set forth in order to provide a thorough understanding of example embodiments. It will be evident, however, to one of ordinary skill in the art that embodiments may be practiced without these specific details.

Generally, a prescription order is generated for a high volume pharmacy. The prescription order may include one or more than one prescription drug for fulfillment. Each prescription drug in a prescription order is an order component of the prescription order. Generally, the order components are pill containers or containers and packaging having a quantity of a prescription drug contained therein.

Dust, debris, tailings and other materials may be generated in connection with packaging pill containers or containers and packaging having a quantity of a prescription drug contained therein for shipment or other delivery to a customer, and a tailing collection device may be deployed to collect and facilitate the disposal of the dust, debris, tailings and other materials.

Figure 1:
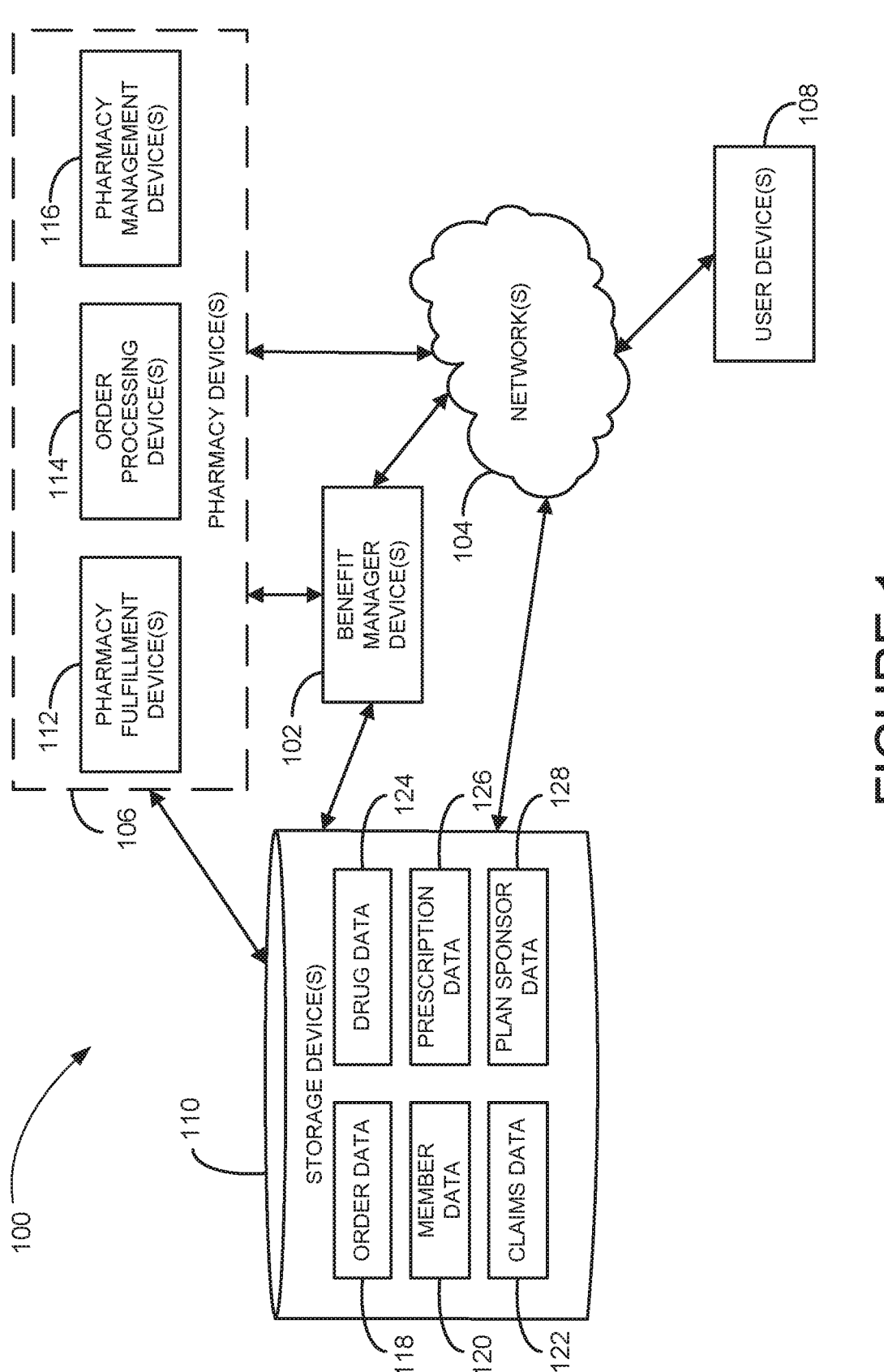
FIG. 1 is a block diagram of an example system, according to an example embodiment.

FIG. 1 is a block diagram of an example implementation of a system 100, according to an example embodiment. While the system 100 is generally described as being deployed in a high volume pharmacy or fulfillment center (e.g., a mail order pharmacy, a direct delivery pharmacy, an automated pharmacy, multiple package delivery center, and the like), the system 100 and/or components thereof may otherwise be deployed (e.g., in a lower volume pharmacy). A high volume pharmacy may be a pharmacy that is capable of filling prescriptions automatically, mechanically, manually, or a combination thereof. The system 100 may include a benefit manager device 102, a pharmacy device 106, and a user device 108, which may communicate with each other directly and/or over a network 104. The system 100 may also include a non-transitory storage device 110.

The benefit manager device 102 is a device operated by an entity that is at least partially responsible for creation and/or management of the pharmacy or drug benefit. While such an entity operating the benefit manager device 102 is typically a pharmacy benefit manager (PBM), other entities may operate the benefit manager device 102 either on behalf of themselves, the PBM, another entity, or other entities. For example, the benefit manager device 102 may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, specialty pharmacies, pharmaceutical vending machines or kiosks, and the like.

Some of the operations of the PBM that operates the benefit manager device 102 may include the following activities and processes. A member (or a person on behalf of the member) of a pharmacy benefit plan administered by or through the PBM attempts to obtain a prescription drug at a retail pharmacy location (e.g., a location of a physical store) from a pharmacist or a pharmacist technician. The member may also attempt to obtain the prescription drug through mail order drug delivery from a mail order pharmacy location, which may be the high volume pharmacy system 100. In some embodiments, the member may also attempt to obtain the prescription drug directly or indirectly through the use of a machine, such as a kiosk, vending unit, mobile electronic device, or a different type of mechanical, electrical, electronic communication device, and/or computing device. Such a machine may be filled with the prescription drug in prescription packaging, which may include multiple prescription components, by the high volume pharmacy system 100.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, or the like. In some instances, an employer of the member may directly or indirectly fund or reimburse the member for the copayments.

The amount of the co-pay required from the member may vary with different pharmacy benefit plans having different plan sponsors or clients and/or prescription drugs. The member's copayment may be based a flat copayment (e.g., $10 or other dollar amounts), coinsurance (e.g., 10% or other percents), and/or a deductible (e.g., for first $500 of annual prescription drug expenses or other dollar amounts) for certain prescription drugs, certain types and/or classes of prescription drugs, and/or all prescription drugs. The copayment may be stored in the non-transitory storage device 110 or determined by the benefit manager device 102.

In some instances, the member may not pay the copayment or may only pay a portion of the copayment for the prescription drug. For example, if the usual and customary cost for a generic version of a prescription drug is $4, and the member's flat copayment is $20 for the prescription drug, the member may only be required to pay $4 to receive the prescription drug. In another example involving a worker's compensation claim, no copayment may be due by the member for the prescription drug.

In addition, copayments may also vary based on different delivery channels used for the prescription drug to be received by the member. For example, the copayment for receiving the prescription drug from a mail order pharmacy location may be less than the copayment for receiving the prescription drug from a retail pharmacy location.

In conjunction with receiving the copayment (if any) from the member and dispensing the prescription drug to the member, the pharmacy submits a claim to the PBM for the prescription drug. After receiving the PBM (e.g., through the benefit manager device 102) may perform certain adjudication operations including verifying eligibility for the member, identifying and/or reviewing an applicable formulary for the member to determine any appropriate copayment, coinsurance, and deductible for the prescription drug, and performing a drug utilization review (DUR) on the member. The PBM provides a response to the pharmacy (e.g. from the benefit manager device 102 to the pharmacy device 106) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on the type(s) of pharmacy network in which the pharmacy is included. Other factors may also be used to determine the amount in addition to the type of pharmacy network. For example, if the member pays the pharmacy for the prescription drug without using the prescription drug benefit provided by the PBM (e.g., by paying cash without use of the prescription drug benefit or by use of a so-called pharmacy discount card offering other negotiated rates), the amount of money paid by the member may be different than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored on the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include an optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Virginia.

Moreover, although the system shows a single network 104, multiple networks can be used. The multiple networks may communicate in series with each other to link the devices 102, 106-110 or in parallel to link the devices 102, 106-110.

The pharmacy device 106 may include an order processing device 114, a pharmacy management device 116, and a pharmacy fulfillment device 112 in communication with each other directly and/or over the network 104.

The order processing device 114 may receive information regarding filling prescriptions and may direct an order component to one or more than one of the devices of the pharmacy fulfillment device 112 at a pharmacy. The pharmacy fulfillment device 112 may fulfill, dispense, aggregate, and/or pack the order components of the prescription drugs in accordance with one or more than one of the prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the pharmacy fulfilment device 112. In some embodiments, the order processing device 114 may be an external device separate from the pharmacy and communicate with other devices located within the pharmacy.

For example, the external order processing device 114 may communicate with an internal order processing device 114 and/or other devices located within the system 100. In some embodiments, the external order processing device 114 may have limited functionality (e.g., as operated by a patient requesting fulfillment of a prescription drug), while the internal order processing device 114 may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together.

The pharmacy management device 116 may enable and/or facilitate management and operations in a pharmacy. For example, the pharmacy management device 116 may provide functionality to enable receipt and processing of prescription drug claims, management of pharmacy personnel, management of pharmaceutical and non-pharmaceutical products, track products in the pharmacy, record workplace incidents involve personnel and products, and the like. In some embodiments, the order processing device 114 may operate in combination with the pharmacy management device 116.

In some embodiments, the pharmacy management device 116 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy management device 116 may be utilized by the pharmacy to submit the claim to the PBM (e.g., through the benefit manager device 102) for adjudication.

In some embodiments, the pharmacy management device 116 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager device 102 may track prescription drug fulfillment and/or other information for patients that are not members or have not identified themselves as members, at the time (or in conjunction with the time) in which they seek to have a prescription filled at a pharmacy.

The pharmacy fulfillment device 112, the order processing device 114, and/or the pharmacy management device

116 may include circuitry, a processor, a memory to store data and instructions, and communication functionality. These devices 112-116, in some embodiments, are dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage) and/or through the network 104 (e.g., by utilizing a cloud configuration or software as a service. etc.) with the non-transitory storage device 110.

The user device 108 is used by a device operator. The device operator may be a user (e.g., an employee, a contractor, a benefit member, a patient of the pharmacy, or the like) associated with the system 100. Other device operators may also operate the user device 108. In some embodiments, the user device 108 may enable the device operator to attend to pharmacy operations in a convenient manner (e.g., remote from a pharmacy). In some embodiments, the user device 108 may enable the device operator to receive information about pharmacy processes, prescription drug fulfillment status, and the like.

The user device 108 may be a stand-alone device that solely provides at least some of the functionality of the methods and systems, or may be a multi-use device that has functionality outside of analysis of the methods and systems. Examples of the user device 108 include a set-top box (STB), a receiver card, a mobile telephone, a personal digital assistant (PDA), a display device, a portable gaming unit, a computing system, and the like. Other devices, however, may also be used. In some embodiments, the computing system may include a mobile computing device. For example, the user device 108 may include a mobile electronic device, such an iPhone or iPad by Apple, Inc., mobile electronic devices powered by Android by Google, Inc., and a Blackberry by Research In Motion Limited. The user device 108 may also include other computing devices, such as desktop computing devices, notebook computing devices, netbook computing devices, gaming devices, and the like. Other types of electronic devices may also be used.

The non-transitory storage device 110 may include: a non-transitory storage (e.g., memory, hard disk, CD-ROM, and the like) in communication with the benefit manager device 102, the pharmacy device 106, and/or the user device 108 directly and/or over the network 104. The non-transitory storage may store order data 118, member 120, claims data 122, drug data 124, prescription data 126, and/or plan sponsor 128. Further, the system 100 may include additional devices, which may communicate with each other directly or over the network 104.

The order data 118 may be related to a prescription order. The order data may include the type of the prescription drug (e.g., drug name and strength) and quantity of the prescription drug. The order data 118 may also include data used for completion of the prescription, such as prescription materials and/or the type and/or size of container in which the drug is dispended or in which is requested to be dispensed. In general, prescription materials include an electronic copy of information regarding the prescription drug for inclusion with or otherwise provided (e.g., via email) in conjunction with the fulfilled prescription. The prescription materials may include electronic information regarding drug interaction warnings, recommended usage, possible side effects, expiration date, date of prescribing, or the like. The order data 118 may be used by the pharmacy to fulfill a pharmacy order.

In some embodiments, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging, and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to facilitate transportation of prescriptions within the pharmacy may also be stored as order data 118.

The member data 120 includes information regarding the members associated with the PBM. The information stored as member data 120 may include personal information, personal health information, protected health information, fitness data, health data, web and mobile app activity, and the like. Examples of the member data 120 include name, address, telephone number, e-mail address, prescription drug history, and the like. The member data 120 may include a plan sponsor identifier that identifies the plan sponsor associated with the member and/or a member identifier that identifies the member to the plan sponsor. The member data 120 may also include, by way of example, dispensation preferences such as type of label, type of cap, message preferences, language preferences, or the like.

The member data 120 may be accessed by various devices in the pharmacy to obtain information utilized for fulfillment and shipping of prescription orders. In some embodiments, an external order processing device 114 operated by or on behalf of a member may have access to at least a portion of the member data 120 for review, verification, or other purposes.

In some embodiments, the member data 120 may include information for persons who are patients of the pharmacy but are not members in a pharmacy benefit plan being provided by PBM. For example, these patients may obtain drug directly from the pharmacy, through a private label service offered by the pharmacy, or otherwise. In general, the use of the terms member (e.g., of a prescription drug benefit plan) and patient (e.g., of a pharmacy) may be used interchangeably in this disclosure.

The claims data 122 includes information regarding pharmacy claims adjudicated by the PBM under a drug benefit program provided by the PBM for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility, and the like. Additional information may be included.

In some embodiments, other types of claims beyond prescription drug claims may be stored in the claims data 122. For example, medical claims, dental claims, wellness claims, or other type of health care-related claims for members may be stored as a portion of the claims data 122.

In some embodiments, the claims data 122 includes claims that identify the members with whom the claims are associated. In some embodiments, the claims data 122 includes claims that have been de-identified (e.g., associated with a unique identifier but not with a particular, identifiable member), aggregated, and/or otherwise processed.

The drug data 124 may include drug name (e.g., technical name and/or common name), other names by which the drug is known by, active ingredients, an image of the drug (e.g., in pill form), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, and the like.

Figure 2:
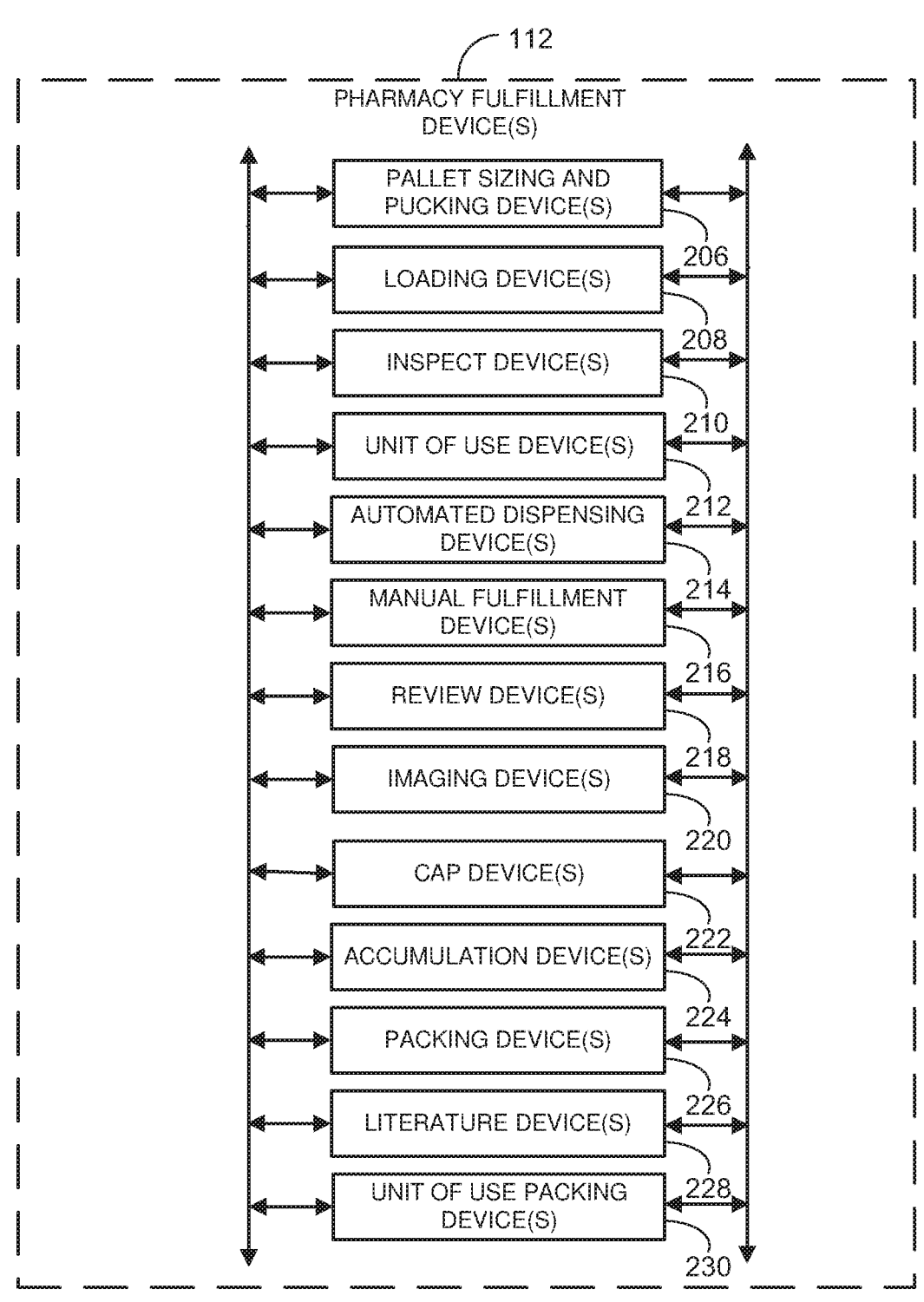
FIG. 2 is a block diagram of an example order processing device that may be deployed within the system of FIG. 1, according to an example embodiment.

FIG. 2 illustrates the pharmacy fulfillment device 112, according to an example embodiment. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the non-transitory storage 110, directly or over the network 104. Specifically, the pharmacy fulfillment device 112 may include pallet sizing and pucking device(s) 206; loading device(s) 208; inspect device(s) 210, unit of use device(s) 212, automated dispensing device(s) 214, manual fulfillment device(s) 216, review device(s) 218, imaging device(s) 220, cap device(s) 222, accumulation device(s) 224, literature device(s) 228, packing device(s) 226, and unit-of-use packing device(s) 230. Further, the pharmacy fulfillment device 112 may include additional devices, which may communicate with each other directly or over the network 104.

In some embodiments, operations performed by one or more of the devices 206-230 may be performed sequentially, or in parallel with the operations of devices as may be coordinated by the order processing device 114. In some embodiments, the order processing device 114 tracks a prescription with the pharmacy based on operations performed by one or more than one of the devices 206-230.

In some embodiments, the pharmacy fulfillment device 112 may transport prescription drug containers, for example, between more than one of the devices 206-230 in the high volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism, or the like. In one embodiment, the loading device 208 has robotic arms or pickers to grasp a prescription container and move it to and from a pallet or to and from a puck. The loading device 208 may also print a label that is appropriate for a container that is to be loaded onto the pallet, and apply the label to the container. The pallet may be located on a conveyor assembly during these operations (e.g., at the high volume fulfillment center or the like).

The inspect device 210 may verify that containers in a pallet are correctly labeled and in the correct spot on the pallet. The inspect device 210 may scan the label on one or more than one container on the pallet. Labels of containers may be scanned or imaged in full or in part by the inspect device 210. Such imaging may occur after the container has been lifted out of its puck by a robotic arm, picker, or the like, or may be otherwise scanned or imaged while retained in the puck. In some embodiments, images and/or video captured by the inspect device 210 may be stored in the non-transitory storage device 110 as a portion of the order data 118.

The unit of use device 212 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, liquids in a spray or other dispensing container, and the like. Prescription drug products dispensed by the unit of use device 212 may be packaged individually or collectively for shipping, or may be shipped in combination with other prescription drugs dispensed by other devices (e.g., in the high volume fulfillment center).

At least some of the operations of devices 206-230 may be directed by the order processing device 114. For example, the manual fulfillment device 216, the review device 218, the automated dispensing device 214, the packing device 226, and/or another device may receive instructions provided by the order processing device 114.

The automated dispensing device 214 may include one or more than one devices that dispense prescription drugs or pharmaceuticals into prescription containers in accordance with one or multiple prescription orders. In general, the automated dispensing device 214 may include mechanical and electronic components with, in some embodiments, software and/or logic to facilitate pharmaceutical dispensing that would otherwise be performed in a manual fashion by a pharmacist and/or pharmacist technician. For example, the automated dispensing device 214 may include high volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high volume fulfillment center.

The manual fulfillment device 216 may provide for manual fulfillment of prescriptions. For example, the manual fulfillment device 216 may receive or obtain a container and enable fulfillment of the container by a pharmacist or pharmacy technician. In some embodiments, the manual fulfillment device 216 provides the filled container to another device in the pharmacy fulfillment device 112 to be joined with other containers in a prescription order for a patient or member. In general, a manual fulfillment may include operations at least partially performed by a pharmacist or a pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter or the like). Prescription drugs dispensed by the manual fulfillment device 216 may be packaged individually or collectively for shipping, or may be shipped in combination with other prescription drugs dispensed by other devices in the high volume fulfillment center.

The review device 218 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review may be performed at the manual station.

The imaging device 220 may image containers prior to filling and/or after they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114, and/or stored in the non-transitory storage device 110 as part of the order data 118.

The cap device 222 may be used to cap or otherwise seal a prescription container. In some embodiments, the cap device 222 may secure a prescription container with a type of cap in accordance with a patient preference (e.g., a preference regarding child resistance, a preference regarding built-in adherence functionality, or the like), a plan sponsor preference, a prescriber preference, or the like. The cap device 222 may also etch a message into the cap or otherwise associate a message into the cap, although this process may be performed by a different device in the high volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218, at the high volume fulfillment center. The accumulation device 224 may be used to group the prescription containers prior to shipment to the member or otherwise.

The literature device 228 prints, or otherwise generates, literature to include with prescription drug orders. The literature may be printed on multiple sheets of substrates, such as paper, coated paper, printable polymers, or combinations thereof. The literature printed by the literature device 228 may include information required to accompany the prescription drugs included in a prescription order, relating to prescription drugs in the order, financial information associated with the order (e.g., an invoice or an account statement, or the like).

In some embodiments, the literature device 228 folds or otherwise prepares the literature for inclusion with a prescription drug order (e.g., in a shipping container or the like). In some embodiments, the literature device 228 that prints the literature may be separate from the literature device that prepares the literature for inclusion with a prescription order. The packing device 226 packages a prescription order in preparation for shipping the order. The packing device 226 may box, bag, or otherwise package the fulfilled prescription order for delivery. The packing device 226 may be a wrap seal device. A wrap seal device deployed as the packing device 226 may pause before an index; during the pause, one or more bottle, envelope or literature item may be placed within a vacuum pocket of the wrap seal device. After any bottle, envelope or literature items have been placed in the pocket, the wrap seal device may index; specifically, the vacuum pocket may move forward. In an example embodiment, the forward movement is about the length of a bag (for example, between about 16 and about 20 inches).

The packing device 226 may further place inserts, (e.g., literature or other papers), into the packaging received from the literature device 228 or otherwise. For example, bulk prescription orders may be shipped in a box, while other prescription orders may be shipped in a bag which may be a wrap seal bag. The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, sort by zip code, or the like). The packing device 226 may include ice or temperature sensitive elements for prescriptions which are to be kept within a temperature range during shipping in order to retain efficacy or otherwise. The ultimate package may then be shipped through postal mail, through a mail order delivery service that ships via ground and/or air (e.g., UPS, FEDEX, or DHL, or the like), through delivery service, through a local delivery service (e.g., a courier service), through a locker box at a shipping site (e.g., an AMAZON locker, library locker, a post office box, or the like), or otherwise.

The unit-of-use packing device 230 packages a unit of use prescription order in preparation for shipping the order. The unit-of-use packing device 230 may include manual scanning of containers to be bagged for shipping to verify each container in the order. In an example embodiment, the manual scanning may be performed at a manual station.

The pharmacy fulfillment device 112 in FIG. may include single devices 206-230 or multiple devices 206-230 (e.g., depending upon implementation in a pharmacy). The devices 206-230 may be the same type or model of device or may be different device types or models. When multiple devices are present, the multiple devices may be of the same device type or models or may be a different device type or model. The types of devices 206-230 shown in FIG. 2 are example devices. In other configurations of the system 100, lesser, additional, or different types of devices may be included.

Moreover, multiple devices may share processing and/or memory resources. The devices 206-230 may be located in the same area or in different locations. For example, the devices 206-230 may be located in a building or set of adjoining buildings. The devices 206-230 may be interconnected (e.g., by conveyors), networked, and/or otherwise in contact with one another or integrated with one another (e.g., at the high volume fulfillment center). In addition, the functionality of a device may be split among a number of discrete devices and/or combined with other devices.

Figure 3A:
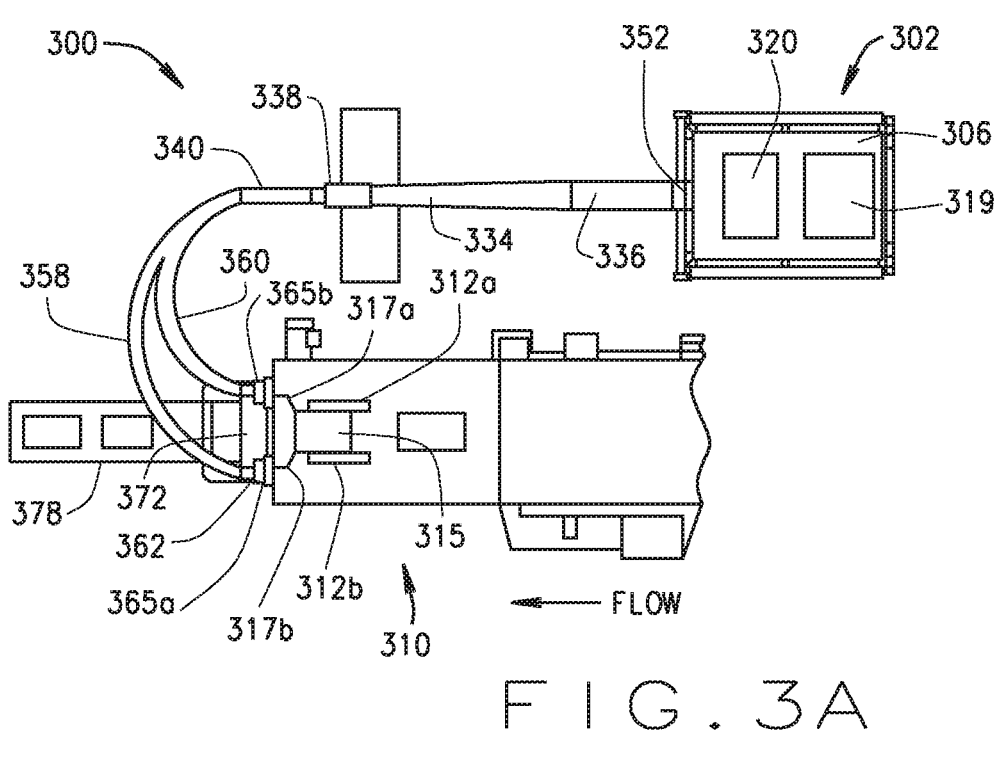
FIG. 3A is a top view of an example tailing collection device that may be deployed within the system of FIG. 1, according to an example embodiment.
Figure 3C:
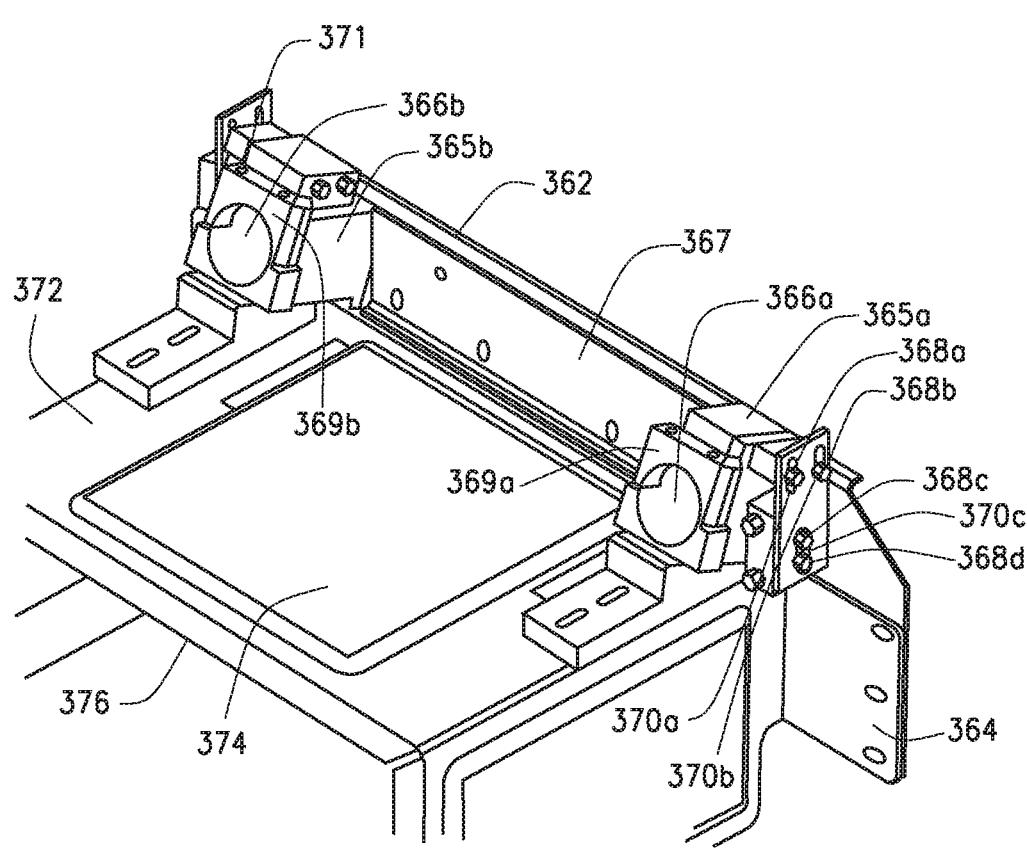
FIG. 3C is a perspective view of a block assembly that may be deployed within the tailing collection device of FIG. 3, according to an example embodiment.
Figures 4, 5, 6, 7:
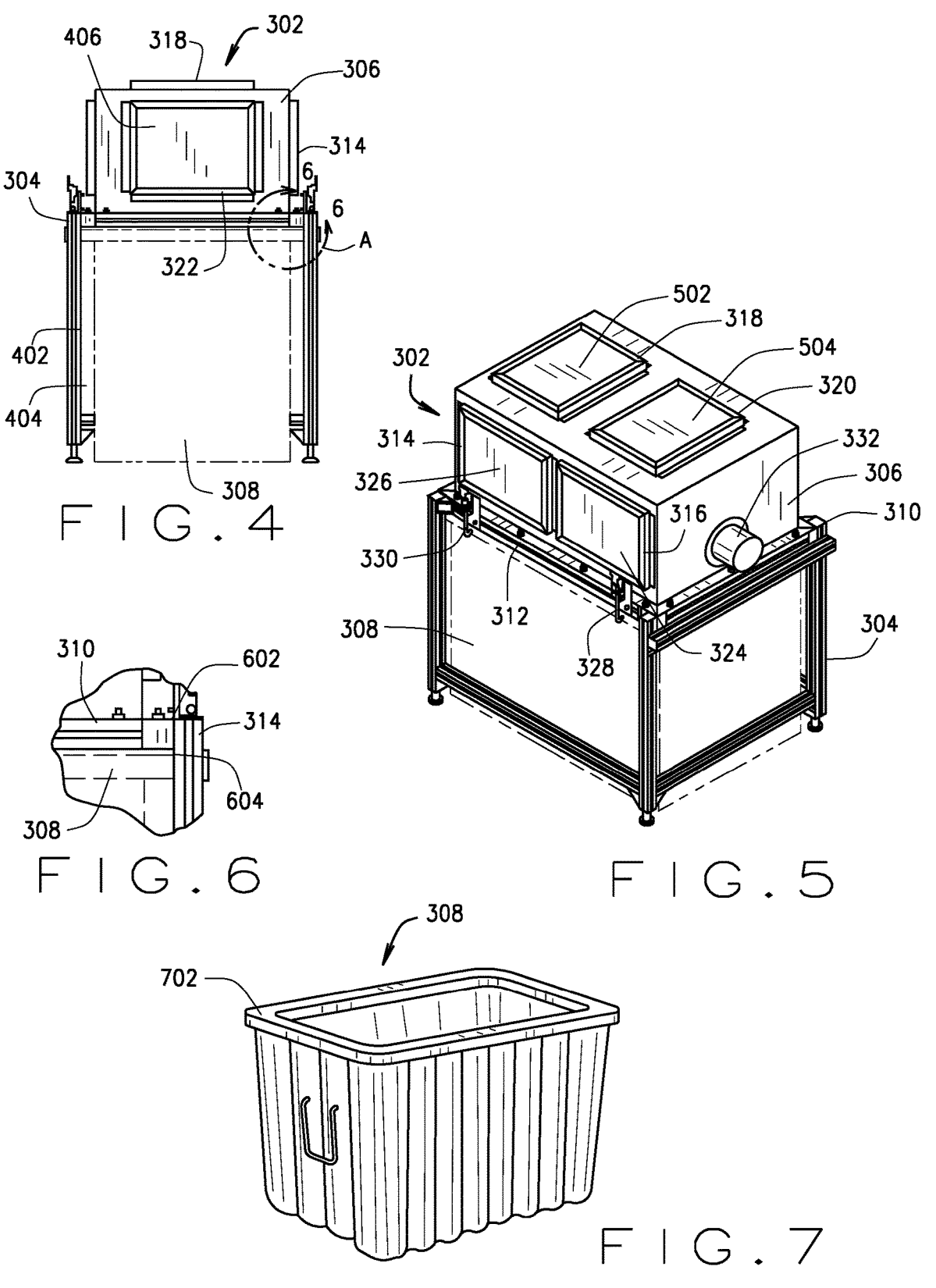
FIG. 4 is an end view of the collection assembly of the tailing collection device of FIG. 3, according to an example embodiment.
FIG. 5 is a side, perspective view of the collection assembly of the tailing collection device of FIG. 3, according to an example embodiment.
FIG. 6 is an detail illustration of a portion of the collection assembly of FIG. 4 taken generally at A, according to an example embodiment.
FIG. 7 is a side, perspective view of a bin that may be deployed within the tailing collection device of FIG. 3, according to an example embodiment.

FIG. 3 illustrates a tailing collection device 300, according to an example embodiment. The tailing collection device 300 can be used with the system 100 or one or more of the device 206-230 of FIGS. 1 and 2, respectively. The tailing collection device 300 may include a collection assembly 302. FIG. 3A illustrates a tailing collection device 300 according to another example embodiment. FIG. 3B illustrates a constricted portion 338 of an intake tube 334 in combination with a blower 342 that may be deployed in the tailing collection devices of FIGS. 3 and 3A. FIG. 3C illustrates a block assembly 362 that may be deployed in the tailing collection device 300 of FIG. 3B. The tailing collection device 300 of FIG. 3 may include a block assembly 362. FIGS. 4 and 5 illustrate additional views of the collection assembly 302 of FIGS. 3 and 3A.

The collection assembly 302 may include a frame 304, a hood 306 and a bin 308. The tailing collection device 300 may be deployed with a packing device 310 and may be adapted to receive debris, dust, or other materials, such as may be generated by the packing device 310, and to facilitate collection and removal of debris, dust, or other materials. The tailing collection device 300 may be otherwise deployed in the system 100 of FIG. 1, or may be otherwise used or deployed.

The packing device 310 may be the packing device 226, the unit-of-use packing device 230 or another packing device, e.g., a packaging device in a high volume fulfillment center. The packing device 310 may be a wrap seal device. For example, a VC999 packaging system manufactured by Inauen Group may be deployed in or as a packing device 310. The packing device 310 may include a rotary cutter 312 adapted to trim edges of a sealed package 315. Tailings 317 may be generated when the edges of the sealed package 315 are trimmed by the rotary cutter 312. Tailings 317 may include the residue left after the trimming of the sealed package 315 is complete. In general, the tailings 317 are not distributed with the sealed package 315 (e.g., for safety or aesthetic purposes).

The frame 304 may include a first end 402 (see FIG. 4) that is adapted to receive the bin 308 into the frame 304. For example, an opening 404 of the first end 402 of the frame 304 may be adapted to receive the bin 308 as it is slid, pushed, or otherwise placed into the frame 304. An opening to receive the bin may be provided in other portions of the frame 304, either instead of or in addition to the opening 404. In an example embodiment, the bin 308 is positioned on the frame 304 above the ground. In an example embodiment, the frame 304 encloses the bin 308 with the bin resting on the floor beneath the frame 304.

The hood 306 may be secured to the frame 304. In an example embodiment, the hood 306 is secured to an upper portion 311 of the frame 304 by one or more fasteners 312, such as, bolts, nuts, pins, screws, and the like. The hood 306 may be otherwise secured to the frame 304. The hood 306 may include one or more than one receptacles 314, 316, 318, 320, 322 adapted to receive filters 324, 326, 406, 502, 504. The filters 324, 326, 406, 502, 504 may be, for example, air filters adapted for use with a home HVAC system. Other air filters may be used as the filters 324, 326, 406, 502, 504 of the tailing collection device 300. In an example embodiment, one or more than one of the filters 324, 326, 406, 502, 504 are approximately 16 inches long, approximately 12 inches wide, and approximately 1 inch thick. The filters may be HEPA industrial filters in an example embodiment. The filters may include filter frames around the perimeter with filtration media supported by the filter frame. The filter frame may be supported in the hood at the receptacles 314, 316, 318, 320, 322. While the filters 324, 326, 406, 502, 504 are shown as generally regular polyhedron, it is within the scope of the present disclosure to use other shapes, e.g., cylindrical filters. In some embodiments, the filters 324, 326, 406, 502, 504 at least substantially cover the receptacles 314, 316, 318, 320, 322. The hood 306 may be formed of metal or other suitable materials, e.g., rigid polymers.

Clamps 328, 330 may be adapted to engage and lift the bin 308, after it has been received within the frame 304, such that the bin 308 engages the upper portion 311 of the frame 304. The clamps 328, 330 may be adjustable hooked rod draw latches, bolts or L-shaped latches. If bolts or L-shaped latches are used as the clamps 328, 330, a mounting plate to receive the bolts or L-shaped latches may be attached to the bin 308.

The hood 306 may include an intake pipe 332. The intake pipe 332 may be adapted to receive an intake tube 334. The intake tube 334 may comprise a first portion 336, a constricted portion 338, and an end portion 340. In some embodiments, the first portion 336 and the end portion 340 may not be constricted relative to the constricted portion. The first portion 336 of the intake tube 334 may be adapted to be received by the intake pipe 332 of the hood 306. In an example embodiment, the first portion 336 is formed of metal, such as aluminum, steel or other suitable metal or alloy that includes one or more metals. In an example embodiment, the first portion 336 is formed of a material, composite, or polymer that is rigid or relatively rigid.

Motive force may be provided within the intake tube to move tailings 317, dust or other debris or materials from the packing device 310, through the intake tube 334 and into the hood 306. The motive force may be air generated by a blower 342. The motive force may be Venturi motive force. The constricted portion 338 may be a Venturi tube provided in combination with a blower 342 to enable achievement of the Venturi effect within the intake tube 334, to cause air and other materials to be pulled through the intake tube 334 and into the hood 306 via the intake pipe 332. The blower 342 may be a ¾ horsepower, 3600 RPM blower. Other blowers may be used as the blower 342. The blower 342 may be selected based on the size, thickness, mass or other quality of the debris, dust or other materials to be collected within the collection assembly 302.

As illustrated in FIG. 3B, an interior tube 352 may be provided within the constricted portion 338. The interior tube 352 may further narrow the interior 354 of the constricted portion 338, thereby enhancing the Venturi effect within the constricted portion 338. The interior tube 352 may terminate at an open first end within the constricted portion and may form or be connected to the end portion 340 of the intake tube 334 at another end, such that tailings 317, dust, debris or other materials flowing through the end portion 340 of the intake tube 334 will flow into and through the first portion 336 of the intake tube 334 via the interior tube 352. In operation, the blower 342 may be deployed to force air through the constricted portion 338. In the embodiment of the constricted portion 338 illustrated in FIG. 3B, air generated by the blower 342 may flow into the interior 354 of the constricted portion 338 at or near the position of the interior tube 352, thereby causing the speed of the air flow within the restricted portion 338 to increase, creating low pressure within the interior tube 352 and the end portion 340 of the intake tube 334, such that the debris, dust or other materials is sucked into and through the intake tube 334 and then pushed by air generated by the blower 342 into the hood 306. In this embodiment, the interior tube 354 is sealed at a position 356 intermediate the blower and the end portion 340, thereby directing the air flow generated by the blower 342 toward the hood 306.

In an example embodiment, the constricted portion 338 in combination with a blower 342 is provided in a horizontal configuration. In an example embodiment, the collection assembly 302 employs positive and negative pressure to remove debris, dust or other materials created within the system 100 without introducing additional valves, dampers, choppers or other moving parts into the flow of product through the system 100.

The end portion 340 of the intake tube 334 may be a semi-rigid or flexible tube suitable for placement at or near a source of debris, dust, or other materials to be collected within the collection assembly 302 of the tailing collection device 300. For example, the end portion 340 may be formed of heavy gauged galvanized flex tubing. Other suitable materials may be employed for the end portion 340 of the intake tube 334 or all or any portions of the intake tube 334.

As illustrated in the embodiment of FIG. 3, the end portion 340 of the intake tube 334 includes a single collection portion. As illustrated in the embodiment of FIG. 3A, the end portion 340 of the intake tube 334 may be configured to include two collection portions 358, 360 of the end portion 340 of the intake tube 334. In other embodiments, more than two collection portions may be included for the end portion 340 of the intake tube.

As illustrated in FIG. 3, when deployed in combination with the packing device 310, the open end of the end portion 340 of the intake tube 334, which is remote from the blower 342, may be placed at or near the rotary cutter 312. When the blower 342 is on, creating the Venturi effect within the intake tube 334, tailings 317, dust and other debris may be sucked into the intake tube 334 and into the hood 306 of the collection assembly 302. The tailing collection device 300 may be otherwise deployed to remove lightweight debris, dust or other materials. In an example, the tailing collection device 300 may be deployed to collect and facilitate removal of lightweight debris, dust or other materials in lieu of a central vacuum system. A central vacuum system may be expensive to install and difficult to maintain relative to the tailing collection device 300.

As illustrated in FIGS. 3A and 3C, in an example embodiment, placement of the open end of the collection portions 358, 360 to collect tailings 317a, 317b and other debris generated when the edges of the sealed package 315 are trimmed by the rotary cutters 312a, 312b may be facilitated by a block assembly 362. The block assembly 362 may include a mounting plate 364 adapted to attach the block assembly 362 to the packing device 310. Receptacles 365a, 365b may be adapted to secure the collection portions 358, 360 of the intake tube 334 within the block assembly 362 and may include an opening 366a, 366b to receive the collection portions 358, 360 of the intake tube. The receptacles 335a, 335b may be adjustable to facilitate placement of the intake tube 334 within the openings 336a, 336b. For example, an upper plate 369a, 369b may be configured to slide upward to facilitate placement of the collection portions 358, 360 within the openings 366a, 366b and may further configured to be secured to hold the collection portions 358, 360 within the openings 366a, 366b of the receptacles 365a, 365b. In an example embodiment, the upper plates 369a, 369b are secured by a bolt 371. The upper plates 369a, 369b may be otherwise secured. The receptacles 365a, 365b may be formed as a part of or affixed to an adjustment plate 367. The adjustment plate 367 may be configured to modify the angle of the receptacles 365a, 365b and the openings 366a, 366b relative to the packing device 310, thereby enabling modification of the angle at which the open portions of the collection portions 358, 360 of the intake tube 334 are placed near the rotary cutters 312a, 312b. For example, adjustment nuts 368a, 368b, 368c, 368d, in combination with adjustment openings 370a, 370b, 370c may be configured to enable adjustment of the angle of the adjustment plate 367 and, therefore, the receptacles 365a, 365b and the openings 366a, 366b, relative to the packing device 310. The block assembly 362 may include a shroud 372 to minimize or prevent access to the rotary cutters 312a, 312b by an operator while in operation. The shroud 372 may reduce the likelihood of operator injury. A window 374 may be included in the shroud 372 to enable an operator to view operation of the tailing collection device 300, including to evaluate its effectiveness at removing the tailings 317a, 317b. The shroud 372 may be open at the end 376 to enable passage of a conveyor 378 to transport the sealed package 315 from the packing device 310. For example, the sealed package 315 may be transported from the packing device 310 to be shipped to customers.

As illustrated in FIG. 6, which is a detail illustration generally at section A of FIG. 4, the upper portion 311 of the frame 304 may include sealant strips 602, 604 adapted to enable the bin 308 to be substantially sealed against the upper portion 311 of the frame 304 when engaged by the clamps 330, 332, 406, such that space formed by the interiors of the bin 308 and the hood 306 is substantially sealed when the bin 308 is engaged by the clamps 328, 330. The sealant strips 602, 604 may be formed of foam, rubber or one or more other materials suitable for sealing. In an example embodiment, sealant strips are natural gum foam strips sold by McMaster-Carr. Sealant strips 602, 604 may be selected based on the ability of the material from which the sealant strips are formed to reduce static electricity generated from plastic, heat and rubbing generated when the tailing collection device 300 is in use.

FIG. 7 illustrates the bin 308 according to an example embodiment. The bin 308 may be formed from one or more than one of polyethylene, metal, nylon, or other suitable materials. In an example embodiment, the bin 308 is a medium duty, polyethylene container. In an example embodiment, the bin is approximately 40 inches long, 28 inches wide, and 30 inches high. Other bins, and bins of other sizes, may be used as the bin 308 of the tailing collection device 300. The bin 308 may include a rim 702 around an upper perimeter of the bin 308. The rim 702 may be adapted to receive the clamps 328, 330 and to form a seal with the upper portion 311 of the frame 304 upon engagement by the clamps 328, 330. The bin 308 is adapted to receive the tailings, other refuse or dust.

Figure 8:
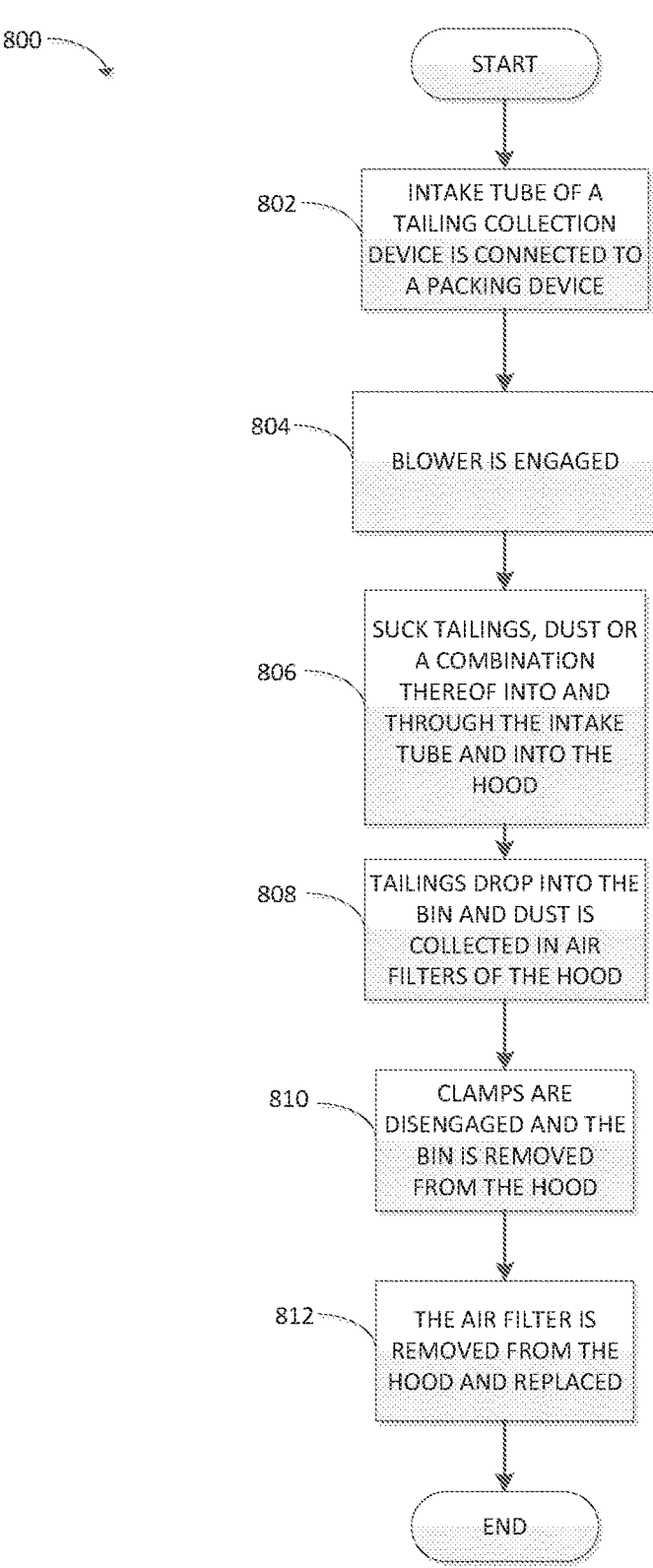
FIG. 8 is an example process flow illustrating a method of collecting and facilitating the removal of tailings and dust generated by a packaging device, according to an example embodiment.

FIG. 8 illustrates a method 800 for removing tailings 317 and dust from a generated by a rotary cutter 312 deployed in packing device 310 within the system 100, wherein the system 100 is deployed in a high volume pharmacy or fulfillment center that is capable of filling prescriptions automatically, mechanically, manually, or a combination thereof. The method 800 may be performed by the tailing collection device 300, partially by the tailing collection device 300, or may be otherwise performed.

At block 802, an intake tube 334 of a tailing collection device 300 is connected to a packing device 310 via a block assembly 362. A blower 342 in communication with the constricted portion 338 of the intake tube 334 is engaged to create the Venturi effect within the constricted portion 338 of the intake tube 334 at block 804. In an example embodiment, the blower 342 is engaged when the packing device 310 indexes. In another example embodiment, the blower 342 is configured to remain on for a pre-determined amount of time. In another embodiment, the blower 342 is configured to be turned on or off by an operator, either with or without automated engagement. At block 806, tailings 317, dust, or a combination thereof are sucked into and through the intake tube 334 and into the hood 306 to which the bin 308 is substantially sealed via clamps 328, 330. At block 808, tailings 317, which are heavy in relation to the dust, drop into the bin 308 and dust is collected in an air filter disposed within the hood 306. At block 810, the clamps 328, 330 are disengaged and the bin 308 is disconnected from the hood 306 and emptied, and at block 812, the air filters are removed from the hood 306 and replaced. In an example embodiment, the blower 342 is turned off before the bin 308 is emptied. In another embodiment, the blower 342 remains on while the bin 308 is emptied.

Figure 9:
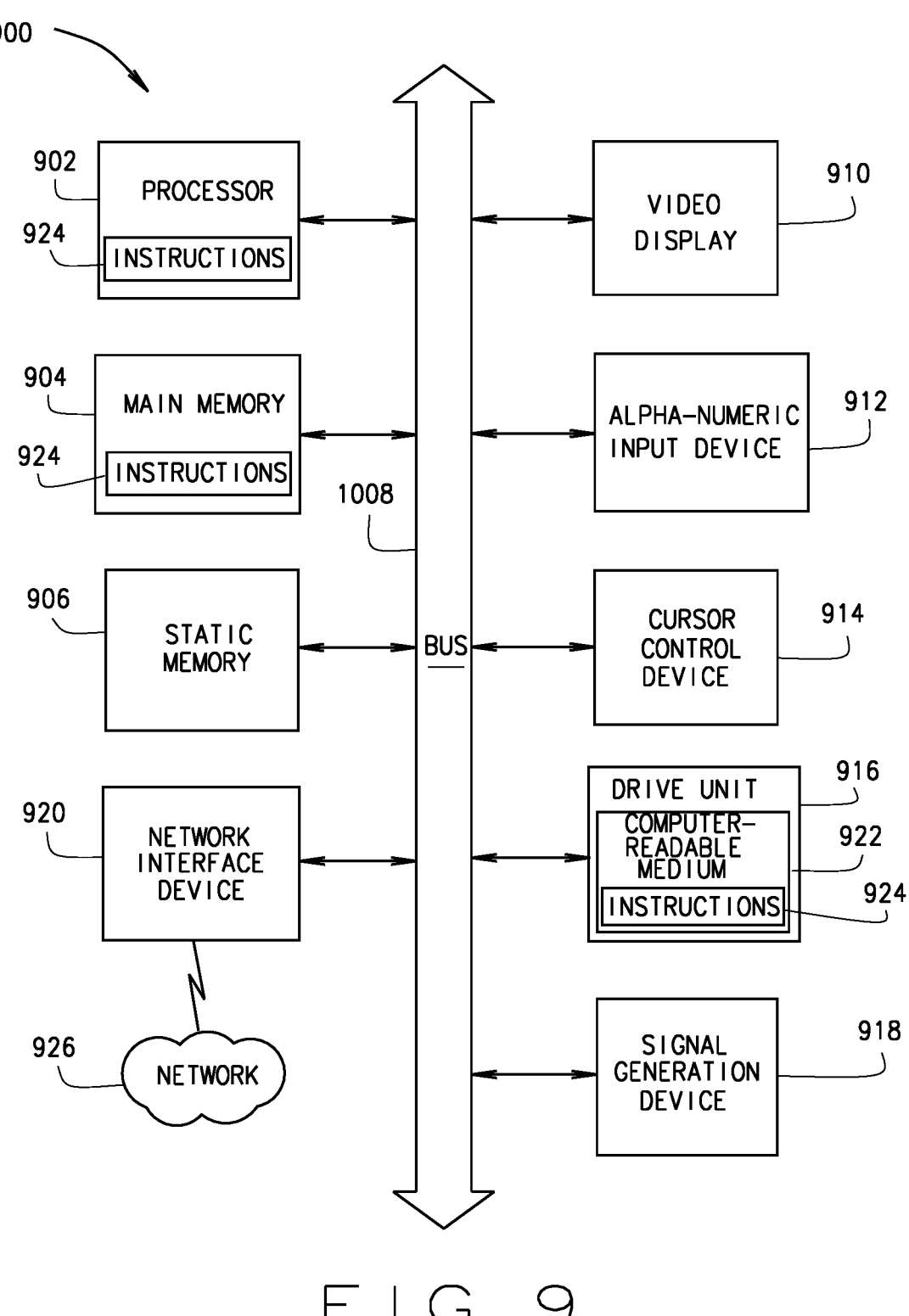
FIG. 9 is a block diagram of a machine in the example form of a computer system within which a set of instructions for causing the machine to perform any one or more of the methodologies discussed herein may be executed or stored.

FIG. 9 shows a block diagram of a machine in the example form of a computer system 900 within which a set of instructions may be executed causing the machine to perform any one or more of the methods, processes, operations, or methodologies discussed herein. The devices 102, 106, 108, 110, 114, 116, 206-230 may include the functionality of the one or more computer systems 900.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specifies actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (e.g., a central processing unit (CPU) a graphics processing unit (GPU) or both), a main memory 904 and a static memory 906, which communicate with each other via a bus 908. The computer system 900 further includes a video display unit 910 (e.g., a liquid crystal display (LCD) or a cathode ray tube (CRT)). The computer system 900 also includes an alphanumeric input device 912 (e.g., a keyboard), a cursor control device 914 (e.g., a mouse), a drive unit 916, a signal generation device 918 (e.g., a speaker) and a network interface device 920.

The drive unit 916 includes a computer-readable medium 922 on which is stored one or more sets of instructions (e.g., software 924) embodying any one or more of the methodologies or functions described herein. The software 924 may also reside, completely or at least partially, within the main memory 904 and/or within the processor 902 during execution thereof by the computer system 900, the main memory 904 and the processor 902 also constituting computer-readable media.

The software 924 may further be transmitted or received over a network 926 via the network interface device 920.

While the computer-readable medium 922 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

In an example embodiment, a pharmaceutical order filling system includes a packing device to package a pharmaceutical order and a tailing collection device deployed in association with the packing device. The packing device is configured to trim an edge of a package containing a pharmaceutical order to generate a tailing and the tailing collection device is configured to collect the tailing. The tailing collection device includes a collection assembly and an intake tube. A portion of the intake tube is constricted and, in combination with a blower, is configured to enable achievement of the Venturi effect within the intake tube. When the Venturi effect is achieved within the intake tube, the tailing is sucked into and through the intake tube into the collection assembly.

In another example embodiment, a method of collecting dust and tailings generated by a cutter of a packing device includes providing a tailing collection device, wherein the tailing collection device includes a collection assembly and an intake tube. The tailing collection device also includes a blower in combination with a constricted portion of the intake tube configured to enable achievement of the Venturi effect within the compressed portion of the intake tube. The open end of the intake tube is placed near the cutter, the blower is engaged to create the Venturi effect within the intake tube, and dust and tailings are received into and through the intake tube and into the collection assembly.

In yet another embodiment, a system includes a packing device and a tailing collection device deployed in association with the packing device. The packing device is configured to trim an edge of a package to generate a tailing and dust, and the tailing collection device is configured to collect the tailing and the dust. The tailing collection device includes a collection assembly and an intake tube. A blower in combination with a constricted portion of the intake tube is configured to enable achievement of the Venturi effect within the intake tube; achievement of the Venturi effect within the intake tube causes the tailing and the dust to be sucked into and through the intake tube into the collection assembly.

The inventive subject matter may be represented in a variety of different embodiments of which there are many possible permutations.

Thus, methods and systems for collecting and facilitating removal of debris, dust and other materials, such as debris, dust or other materials generated by a packing device or a unit of use packing device, are described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium.

The invention claimed is:

1. A dispensing system comprising:
a dispenser to fill a pharmaceutical container with a drug;
a packing device to package a pharmaceutical container for shipment in a sealed package and to move the sealed package in a flow direction; and
a cutter including at least two cutters that are configured to cut, in a direction aligned with the flow direction, a longitudinal edge of the sealed package containing the pharmaceutical container to generate a tailing; and
a tailing collection device, deployed in association with the cutter, including a collection assembly, an intake tube connected to the collection assembly, and a blower configured to enable a motive force within the intake tube to transport the tailing into the intake tube to the collection assembly, wherein the intake tube includes an adjustment plate at an open end of the intake tube.

2. The dispensing system of claim 1, wherein the open end is adjacent the cutter, and the sealed package is one of a plurality of sealed packages connected to each other in the flow direction, and wherein the open end is configured to remove the tailing from adjacent the sealed package with the sealed package being free from the tailing for distribution.

3. The dispensing system of claim 2, wherein the packing device forms the sealed package as a wrap seal package.

4. The dispensing system of claim 2, wherein the packing device moves the plurality of sealed packages, which contain different pharmaceutical orders respectively, in the flow direction past the cutter to produce the tailing.

5. The dispensing system of claim 1, wherein the dispensing system includes a unit of use dispenser to select a unit of use according to a pharmaceutical order and place the unit of use in a package according to a pharmaceutical order before sealing.

6. The dispensing system of claim 1, wherein the dispensing system is configured to insert a temperature sensitive element in a package prior to sealing to create the sealed package when the drug is temperature sensitive.

7. The dispensing system of claim 1, wherein the packing device indexes successive packages prior to sealing with the successive packages being connected together, wherein the cutter creates the tailing, and wherein the intake tube removes the tailing from adjacent the two or more of the successive sealed packages with the successive sealed packages being free from the tailing for distribution.

8. The dispensing system of claim 1, wherein the intake tube includes a first inlet and a second cutter respectively adjacent to a first cutter and the second cutter of the at least two cutters, wherein the first cutter creates a first tailing, wherein the second cutter creates a second tailing, and wherein the intake tube includes a first inlet that removes the first tailing from the first side of the two or more of the successive sealed packages with the successive sealed packages being free from the first tailing for distribution and a second inlet that removes the second tailing from the second side of the two or more of the successive sealed packages with the successive sealed packages being free from the second tailing for distribution.

9. A method of preparing pharmaceutical orders, comprising:

filling, using a drug dispenser, a pharmaceutical container with a drug according to a pharmaceutical order;

packaging, with a packaging device, the pharmaceutical container with associated literature into a packaging bag for shipping;

sealing the packaging bag;

placing an open end of an intake tube of a tailing collection device near a cutter of the packing device;

moving a sealed packaging bag in a flow direction toward and past the cutter;

cutting an edge of the sealed packaging bag with the cutter along the flow direction to separate a tailing from the sealed packaging bag;

engaging a blower of the tailing collection device to create a motive force within the intake tube to draw the tailing into the intake tube; and receiving the tailing into and through the intake tube and into a collection assembly, wherein placing the open end of the intake tube of the tailing collection device includes positioning an adjustment plate fixed to an intake end of the intake tube.

10. The method of claim 9, wherein engaging the blower includes forcing air through a constricted portion of the intake tube configured to generate the motive force within the intake tube whereby causing the tailing to be sucked into and through the intake tube into the collection assembly.

11. The method of claim 10, wherein engaging the blower of the tailing collection device forms a Venturi in the intake tube and wherein the receiving the tailing includes receiving dust from adjacent the sealed packaging bag.

12. The method of claim 9, wherein engaging the blower of the tailing collection device includes forcing air flow in a restricted portion of the intake tube to generate the motive force to move the tailing into the intake tube away from the sealed package at an angle relative to the sealed package.

13. The method of claim 12, wherein receiving the tailing includes delivering the tailing to a removable bin.

14. A method of preparing pharmaceutical orders, comprising:

filling, using a drug dispenser, a pharmaceutical container with a drug according to a pharmaceutical order;

packaging, with a packaging device, the pharmaceutical container with associated literature into a packaging bag for shipping;

sealing the packaging bag;

placing an open end of an intake tube of a tailing collection device near a cutter of the packing device;

moving a sealed packaging bag in a flow direction toward and past the cutter;

cutting an edge of the sealed packaging bag with the cutter along the flow direction to separate a tailing from the sealed packaging bag;

engaging a blower of the tailing collection device to create a motive force within the intake tube to draw the tailing into the intake tube;

receiving the tailing into and through the intake tube and into a collection assembly;

wherein engaging the blower of the tailing collection device includes forcing air flow in a restricted portion of the intake tube to generate the motive force to move the tailing into the intake tube away from the sealed package at an angle relative to the sealed package; and wherein receiving the tailing includes delivering the tailing through a fixed hood and then into a removable bin after the removable bin has been lofted and fluidly secured to the fixed hood to define an enclosed space.

15. The method of claim 14, wherein placing the open end of the intake tube of the tailing collection device includes positioning an adjustment plate fixed to an intake end of the intake tube.

16. The method of claim 14, wherein cutting includes singulating the sealed package from a continuous flow of connected material for a plurality of sealed packages.

17. A method of preparing pharmaceutical orders, comprising:

filling, using a drug dispenser, a pharmaceutical container with a drug according to a pharmaceutical order;

packaging, with a packaging device, the pharmaceutical container with associated literature into a packaging bag for shipping;

wrap sealing the packaging bag;

placing an open end of an intake tube of a tailing collection device near a cutter of the packing device;

moving a sealed package in a flow direction toward and past the cutter;

cutting an edge of the sealed package with the cutter along the flow direction to separate a tailing from the sealed packaging bag;

engaging a blower of the tailing collection device to create a motive force within the intake tube to draw the tailing into the intake tube; and receiving the tailing into and through the intake tube and into a collection assembly, wherein placing the open end of the intake tube of the tailing collection device includes positioning an adjustment plate fixed to an intake end of the intake tube.

18. The method of claim 17, wherein wrap sealing includes indexing wrap seal bag portions to place the pharmaceutical container in a bottom pocket of the wrap seal packaging bag and then wrap sealing the bottom pocket with a top seal to form the wrap seal bag with the tailing being at least part of at least one of the bottom pocket, the top seal, or both.

* * * * *